(12) United States Patent
Brackhagen et al.

(10) Patent No.: US 11,000,594 B2
(45) Date of Patent: May 11, 2021

(54) COMPOSITION COMPRISING AN ORGANIC LIQUID DILUENT AND A CELLULOSE ETHER OF VERY LOW VISCOSITY

(71) Applicant: Dow Global Technologies LLC, Midland, MI (US)

(72) Inventors: Meinolf Brackhagen, Walsrode (DE); Nicholas S. Grasman, Midland, MI (US); Mark J. Hall, Gaylord, MI (US); Steven J. Guillaudeu, Midland, MI (US); Robert L. Schmitt, Annandale, NJ (US); Matthias Knarr, Nienburg/Weser (DE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/357,687

(22) Filed: Mar. 19, 2019

(65) Prior Publication Data

US 2019/0209693 A1    Jul. 11, 2019

Related U.S. Application Data

(62) Division of application No. 15/292,914, filed on Oct. 13, 2016, now Pat. No. 10,272,156, which is a division of application No. 14/413,080, filed as application No. PCT/US2013/050216 on Jul. 12, 2013, now abandoned.

(60) Provisional application No. 61/672,411, filed on Jul. 17, 2012.

(51) Int. Cl.
| | | |
|---|---|---|
| *A61K 9/10* | (2006.01) | |
| *A61K 47/38* | (2006.01) | |
| *A61K 9/16* | (2006.01) | |
| *A61K 9/28* | (2006.01) | |
| *C08L 1/28* | (2006.01) | |
| *A61K 9/14* | (2006.01) | |
| *A61K 31/343* | (2006.01) | |
| *A61K 31/4166* | (2006.01) | |

(52) U.S. Cl.
CPC ............ *A61K 47/38* (2013.01); *A61K 9/10* (2013.01); *A61K 9/146* (2013.01); *A61K 9/1652* (2013.01); *A61K 9/2866* (2013.01); *A61K 31/343* (2013.01); *A61K 31/4166* (2013.01); *C08L 1/284* (2013.01)

(58) Field of Classification Search
CPC .. A61K 31/343; A61K 31/4166; A61K 47/38; A61K 9/10; A61K 9/146; A61K 9/1652; A61K 9/2866; C08L 1/284
See application file for complete search history.

(56) References Cited

U.S. PATENT DOCUMENTS

| | | | |
|---|---|---|---|
| 2,748,111 A | 5/1956 | Grassi et al. | |
| 3,477,864 A | 11/1969 | Tuji | |
| 3,769,247 A | 10/1973 | Grover et al. | |
| 3,853,988 A | 12/1974 | Casadio et al. | |
| 4,061,859 A | 12/1977 | Cheng | |
| 4,302,440 A | 11/1981 | John et al. | |
| 5,054,511 A | 10/1991 | Tuan et al. | |
| 7,070,828 B2 | 7/2006 | Sheskey et al. | |
| 9,763,874 B2 * | 9/2017 | Pisani | A61P 35/00 |
| 10,016,372 B2 * | 7/2018 | Singh | A61K 47/02 |
| 10,052,406 B2 * | 8/2018 | Ren | A61L 27/54 |
| 2005/0042290 A1 | 2/2005 | Kerc et al. | |
| 2008/0260837 A1 | 10/2008 | Namburi et al. | |
| 2009/0028938 A1 | 1/2009 | Berndl et al. | |
| 2013/0243870 A1 | 9/2013 | Abe et al. | |

FOREIGN PATENT DOCUMENTS

| | | |
|---|---|---|
| EP | 0872233 A1 | 10/1998 |
| EP | 2647648 A1 | 10/2013 |
| JP | 2012116811 A | 6/2012 |
| WO | WO-01/85135 A1 | 11/2001 |
| WO | WO-03/048147 A2 | 6/2003 |
| WO | WO-2005115330 A2 | 12/2005 |
| WO | WO-2005118649 A1 | 12/2005 |
| WO | WO-2007145709 A1 | 12/2007 |
| WO | WO-2009061815 A1 | 5/2009 |
| WO | WO-2009061821 A2 | 5/2009 |

OTHER PUBLICATIONS

Bee et al., Insolubility solved by spray drying. Retrieved from the Internet on Jul. 27, 2017 [URL: <https://www.manufacturingchemist.com/technical/article_page/Insolubility_solved_by_spray_drying/4661 8>] (6 pages) (2010).
Bevernage et al., Excipient-Mediated Supersaturation in human Intestinal Fluids. Mol Pharm. 2011;8:564-70.
Brietenbach, Melt extrusion: from process to drug delivery technology. Eur J Pharm Biopharm. 2002; 34:107-17.
Curatolo et al., Utility of Hydroxypropylmethylcellulose Acetate Succinate (HPMCAS) for nitiation and Maintenance of Drug Superstition in the GI Milieu. Pharm Res. 2009; 26(6):1419-31.
Dow Methocel Technical Handbook. Retrieved on Apr. 1, 2018 from the Internet [URL: <http://msdssearch.dow.com/PublishedLiteratureDOWCOM/dh096d/0901b8038096d9ff.pdf?fllepath-methocel/pdfs/noreg/192-01062.pdf&fromPage=GetDoc>] (2002).
Friesen et al., Hydroxypropyl Methylcellulose Acetate Succinate-Based Spray-Dried Dispersions: An Overview. Mol Pharm. 2008; 5(6):1003-19.

(Continued)

*Primary Examiner* — Ernst V Arnold

(57) ABSTRACT

A liquid composition which comprises an organic liquid diluent and at least one non-ionic cellulose ether having a viscosity of up to 2.33 mPa·s, measured as a 2 wt.-% solution in water at 20° C., is stable over an extended time period. The liquid composition is useful for preparing a solid dispersion comprising at least one active ingredient in at least one cellulose ether by spray-drying. Alternatively a solid dispersion can be produced by blending and extruding at least one active ingredient, at least one cellulose ether having a viscosity of up to 2.33 mPa·s and optionally one or more adjuvants.

11 Claims, No Drawings

(56) References Cited

OTHER PUBLICATIONS

Hodges et al., Determination of Alkoxyl Substitution in Cellulose Ethers by Zeisel Gas Chromatography. Anal Chem. 1979; 51(13):2172-6.
Motrin® (Ibuprofen). Retrieved from the Internet [URL: <https://www.accessdata.fda.gov/drugsatfda_docs/label/2007/019842s020lbl.pdf>] (2006).
Raghavan et al., Crystallization of hydrocortisone acetate: influence of polymers. Int J Pharm. 2001; 212:213-21.
Shose and Cripppen, Atomic Physicochemical Parameters for Three Dimensional Structure Directed Quantitative Structure-Activity Relationships. 2. Modeling Dispersive and Hydrophobic Interactions. J Chem Inf Comput Sci. 1987; 27:21-35.
Van de Mooter, The use of amorphous solid dispersions: A formulation strategy to overcome poor solubility and Jissolution rate. Drug Discov Today. 2011;xxx(xx):e1-7.
Viswanashan et al., Atomic Physicochemical Parameters for Three Dimensional Structure Directed Quantitative Structure-Activity Relationships. 4. Additional Parameters for Hydrophobic and Dispersive Interactions and Their Application for an Automated Superposition of Certain Naturally Occurring Nucleoside Antibiotics. J Chem Inf Comput Sci. 1989; 29:163-72.
Warren et al., Using polymeric precipitation inhibitors to improve the absorption of poorly water-soluble drugs: A mechanistic basis for utility. J Drug Targeting. 2010; 18(10):704-31.

\* cited by examiner

COMPOSITION COMPRISING AN ORGANIC LIQUID DILUENT AND A CELLULOSE ETHER OF VERY LOW VISCOSITY

CROSS-REFERENCE TO RELATED APPLICATIONS

This application is a division of U.S. patent application Ser. No. 15/292,914, filed Oct. 13, 2016, which is a division of U.S. patent application Ser. No. 14/413,080, filed Jan. 6, 2015, which is a U.S. National Phase Application of International Application No. PCT/US2013/050216, filed Jul. 12, 2013, which claims the benefit of U.S. Provisional Patent Application No. 61/672,411, filed Jul. 17, 2012, each of which are hereby incorporated by reference in their entirety.

FIELD

This invention relates to a liquid composition comprising an organic liquid diluent and a cellulose ether and to a solid dispersion comprising an active ingredient in a cellulose ether.

INTRODUCTION

A large number of presently known drugs have a low solubility in water, and thus complex techniques are required to prepare a suitable dosage form. Much research is spent on the use of pharmaceutically acceptable water-soluble polymers in combination with drugs of low water solubility. The use of water-soluble polymers aims at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon administration. However, simple blending of a water-soluble polymer with a drug of low water solubility generally does not reduce the crystallinity of the drug nor generally improve said drug's solubility.

G. Van den Mooter, "The use of amorphous solid dispersions: A formulation strategy to overcome poor solubility and dissolution rate", *Drug Discov Today: Technol* (2011), doi:10.1016/j.ddtec.2011.10.002, discusses the preparation of amorphous solid dispersions to increase the bioavailability of poorly soluble drugs by improving their rate and extent of dissolution. The two most applied manufacturing methods for preparing amorphous solid dispersions are said to be spray drying and extrusion, typically hot melt extrusion. The former process starts from a solution of the drug and a carrier in a common organic solvent or mixture of aqueous and organic solvents. This solution is atomized using a nozzle and the solvent is subsequently quickly evaporated (order of magnitude is milliseconds). The very fast solvent evaporation contributes to the amorphous state of the solid dispersion.

Dallas B. Warren et al. (*Journal of Drug Targeting*, 2010; 18(10): 704-731) have studied the use of water-soluble cellulose ethers as polymeric precipitation inhibitors, such as carboxymethyl cellulose (CMC), methyl cellulose (MC), hydroxyethyl cellulose (HEC), and hydroxypropylmethyl cellulose (HPMC) to improve the absorption of poorly water-soluble drugs.

S. L. Raghavan et al. (International Journal of Pharmaceutics 212 (2001) 213-221), have studied the influence of HPMC, MC, polyvinyl pyrrolidone (PVP) and polyethylene glycol (PEG400) on the crystallization of hydrocortisone acetate (HA).

International Patent Application WO2008/047201 discloses solid dispersions which comprise a poorly water soluble ionizable drug, a cationic species, and a dispersion polymer, such as hydroxypropyl methylcellulose (HPMC). According to the examples a drug and HPMC (E3 Prem LV; Methocel®, available from The Dow Chemical Company, Midland, Mich.) are mixed with water and methanol to form spray solutions. Solid spray-dried dispersions of the drug in HPMC are produced from this solution.

Unfortunately, compositions comprising an organic liquid diluent and a cellulose ether often are not storage stable but exhibit a huge viscosity increase after storage of the liquid composition over an extended time period. The viscosity increase can often be avoided by storing the liquid composition below room temperature, but this is often undesirable since it complicates storage and adds to storage costs. Moreover, the observed viscosity increase often limits the achievable content of the cellulose ether in the liquid composition, thus adding transportation and solvent recovery costs.

In view of the high importance and large number of poorly water soluble drugs, it is an object of the present invention to provide new liquid compositions which comprise an organic liquid diluent and a cellulose ether into which active ingredients can be incorporated, such as poorly water-soluble drugs, and which can be spray-dried to produce solid dispersions comprising an active ingredient in a cellulose ether. A preferred object of the present invention is to provide new liquid compositions comprising an organic liquid diluent and a cellulose ether which are more storage stable than known comparable liquid compositions comprising an organic liquid diluent and at a cellulose ether. It is another preferred object of the present invention to find new liquid compositions comprising an organic liquid diluent and a cellulose ether which increase the solubility of an active ingredient in spray-dried solid dispersions produced therefrom.

SUMMARY

Surprisingly, it has been found that the storage stability of liquid compositions comprising an organic liquid diluent and a non-ionic cellulose ether can be increased if a cellulose ether of very low viscosity is incorporated into the liquid composition.

Accordingly, one aspect of the present invention is a liquid composition which comprises an organic liquid diluent and at least one non-ionic cellulose ether having a viscosity of up to 2.33 mPa·s, measured as a 2 wt.-% solution in water at 20° C.

Another aspect of the present invention is the use of the liquid composition as defined above for preparing a solid dispersion comprising at least one active ingredient in at least one cellulose ether.

Yet another aspect of the present invention is a solid dispersion comprising at least one active ingredient in at least one cellulose ether, wherein the cellulose ether has a viscosity of up to 2.33 mPa·s, measured as a 2 wt.-% solution in water at 20° C.

Yet another aspect of the present invention is a process for producing the solid dispersion, which comprises the steps of blending a) at least one cellulose ether having a viscosity of up to 2.33 mPa·s, measured as a 2 wt.-% solution in water at 20° C., b) one or more active ingredients and c) one or more optional additives, and subjecting the blend to extrusion.

Yet another aspect of the present invention is a process for producing the solid dispersion, which process comprises the steps of providing the liquid composition as defined above and removing liquid diluent from the liquid composition.

Yet another aspect of the present invention is a process for coating a dosage form which comprises the step of contacting the liquid composition as defined above with the dosage form.

Yet another aspect of the present invention is a process for the manufacture of capsules which comprises the step of contacting the liquid composition as defined above with dipping pins.

DETAILED DESCRIPTION

The liquid composition of the present invention comprises at least one cellulose ether having a viscosity of up to 2.33 mPa·s, preferably from 1.20 to 2.26 mPa·s, more preferably from 1.20 to 2.00 mPa·s, most preferably from 1.20 to 1.80, measured as a 2 wt.-% solution in water at 20° C. It is understood that the viscosity values set forth herein are determined as a 2% by weight cellulose ether solution in water at 20° C. The 2% by weight cellulose ether solution in water is prepared according to United States Pharmacopeia (USP 35, "Hypromellose", pages 3467-3469) followed by an Ubbelohde viscosity measurement according to DIN 51562-1:1999-01 (January 1999).

The cellulose ether is non-ionic and generally water-soluble. A water-soluble cellulose ether is a cellulose ether that has a solubility in water of at least 2 grams in 100 grams of distilled water at 25° C. and 1 atmosphere. The non-ionic cellulose ether preferably is a hydroxyalkyl alkylcellulose or an alkylcellulose. Nonlimiting examples of non-ionic water soluble cellulose ethers include $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, mixed $C_1$-$C_3$-alkyl celluloses, such as methyl ethyl celluloses, or ternary cellulose ethers, such as ethyl hydroxypropyl methyl celluloses, ethyl hydroxyethyl methyl celluloses, hydroxyethyl hydroxypropyl methyl celluloses, or alkoxy hydroxyethyl hydroxypropyl celluloses, the alkoxy group being straight-chain or branched and containing 2 to 8 carbon atoms.

In an embodiment, the cellulose ether is methylcellulose, hydroxyethyl cellulose, hydroxypropyl cellulose, hydroxyethyl methylcellulose, hydroxypropyl methylcellulose, hydroxybutyl methylcellulose, or ethylhydroxyethyl cellulose. Preferably the cellulose ether is a hydroxypropyl methylcellulose (HPMC) or a methylcellulose (MC).

The cellulose ether preferably has a DS(alkyl) of from 1.0 to 2.5, more preferably from 1.1 to 2.4, most preferably from 1.5 to 2.2, and particularly from 1.6 to 2.05. The degree of the alkyl substitution, DS(alkyl), of a cellulose ether is the average number of OH groups substituted with alkyl groups, preferably methyl groups per anhydroglucose unit. For determining the DS(alkyl), the term "OH groups substituted with alkyl groups" does not only include the alkylated OH groups directly bound to the carbon atoms of the cellulose backbone but also alkylated OH groups that have been formed after hydroxyalkylation.

The cellulose ether generally has an MS(hydroxyalkyl) of 0 to 1.10, preferably 0.05 to 0.90, more preferably 0.12 to 0.75, most preferably 0.15 to 0.60, and particularly 0.21 to 0.50. The degree of the hydroxyalkyl substitution is described by the MS (molar substitution). The MS(hydroxyalkyl) is the average number of hydroxyalkyl groups which are bound by an ether bond per mole of anhydroglucose unit. During the hydroxyalkylation, multiple substitutions can result in side chains.

The term "hydroxyl group substituted with alkyl group" or "hydroxyl group substituted with hydroxyalkyl group" as used herein means that the hydrogen atom on the hydroxyl group is replaced by an alkyl group or a hydroxyalkyl group.

The sum of the MS(hydroxyalkyl) and the DS(alkyl) preferably is at least 1.5, more preferably at least 1.7, most preferably at least 1.9, and preferably up to 2.9, or up to 2.7, or up to 2.5.

The determination of the % methoxyl in methylcellulose (MC) is carried out according to the United States Pharmacopeia (USP35, "Methylcellulose", pages 3868-3869). The determination of the % methoxyl and % hydroxypropoxyl in hydroxypropyl methylcellulose (HPMC) is carried out according to the United States Pharmacopeia (USP 35, "Hypromellose", pages 3467-3469). The values obtained as % methoxyl and % hydroxypropoxyl are subsequently converted into degree of substitution (DS) for methyl substituents and molar substitution (MS) for hydroxypropyl substituents. Residual amounts of salt are taken into account in the conversion. Based on these methods, the skilled artisans know how to determine MS(hydroxyalkyl) and DS(alkyl) of other cellulose ethers.

The determination of the ether substitution of other ethers than methylcellulose and hydroxypropyl methylcellulose, such as hydroxyethyl methylcellulose (HEMC), can be effected as described by K. L. Ketterer, W. E. Kester, D. L. Wiederrich, and J. A. Grover, Determination of Alkoxyl Substitution in Cellulose Ethers by Zeisel-Gas Chromatographie, Analytical Chemistry, Vol. 51, No. 13, November 1979, 2172-76.

The above-described cellulose ethers and their production are described in the international patent application WO2009061821A2.

The composition of the present invention is liquid at 25° C. and atmospheric pressure and comprises an organic liquid diluent, in addition to at least one cellulose ether as described above. The term "organic liquid diluent" as used herein means an organic solvent or a mixture of two or more organic solvents that is liquid at 25° C. and atmospheric pressure. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The liquid composition of the present invention may additionally comprise water; however, the liquid composition should comprise more than 50, more preferably at least 65, and most preferably at least 75 weight percent of an organic liquid diluent and less than 50, more preferably up to 35, and most preferably up to 25 weight percent of water, based on the total weight of the organic liquid diluent and water. Specific examples of preferred organic liquid diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acrylonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

The liquid composition of the present invention comprising an organic liquid diluent and an above-described cellulose ether has been found to be surprisingly stable upon storage. It has been found that a liquid composition comprising an above-described cellulose ether having a viscosity of up to 2.33 mPa·s, measured as a 2 wt.-% solution in water at 20° C., is more storage stable and exhibits a smaller viscosity increase after storage of the liquid composition over an extended time period than a liquid composition comprising an organic liquid diluent and a comparable cellulose ether having a higher viscosity. When the liquid composition of the present invention comprises an organic liquid diluent and 10 weight percent of the above-described cellulose ether, based on the total weight of the liquid composition, its viscosity at 25° C. 30 minutes after its preparation typically is in the range of 10 to 4000 mPa·s, more typically of 50 to 1500 mPa·s, most typically 100 to 1000 mPa·s, measured as indicated above. When such liquid composition of the present invention, which comprises 10 weight percent of the above-described cellulose ether, is stored for at least 16 hours at 25° C., typically the viscosity of the liquid composition is not more than the 15-fold viscosity, more typically not more than the 10-fold viscosity of the liquid composition at 25° C. 30 minutes after the liquid composition has been prepared. Accordingly, the liquid composition of the present invention comprising an organic liquid diluent and an above-described cellulose ether does not tend to undesired viscosity increase upon storage at room temperature. The reduced tendency to viscosity increase allows a higher concentration of at least one above-described cellulose ether in a liquid composition comprising an organic liquid diluent while still preserving the flowability of the liquid composition. The increased storage stability is of particular importance if the composition of the present invention is directly used in liquid form, for example in the form of a suspension, a sprayable composition, or a syrup as described further below. However, the increased storage stability is also of high importance if the liquid diluent is removed from the liquid composition to produce various dosage forms as described further below. The increased storage stability increases the processing window, i.e., the possible time period from the preparation of the liquid composition until its further processing.

The liquid composition of the present invention is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the liquid composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers.

The cellulose ethers comprised in the liquid compositions of the present invention and in the solid dispersions of the present invention are able to maintain the concentration of poorly water-soluble active ingredients, such as poorly water-soluble drugs in aqueous solutions at supersaturation levels. A considerably higher concentration of a poorly water-soluble active ingredient in an aqueous solution can be maintained than in the absence of a cellulose ether described above. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P. The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J.Chem.Inf.Comput.Sci. 2 1 (1987)); Viswanadhan's fragmentation method (29 J.Chem.Inf.Comput.Sci. 163 (1989)); or Broto's fragmentation method (19 Eur.J.Med.Chem.-Chim.Theor. 7 1 (1984)).

$$\log P_{oct/wat} = \log\left(\frac{[solute]_{octanol}}{[solute]_{water}^{un-ionized}}\right)$$

Compounds with high log P values are very hydrophobic and tend to have extremely low water solubilities (often less than 1 μg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25-1.4) and low to moderate log P values (less than about 6). Compounds in Group 3 have even higher Tm/Tg values (greater than 1.4) and low to moderate log P values (less than about 6). Finally, Group 4 compounds have high log P values (at least about 6).

A preferred aspect of the present invention is a liquid composition or a solid dispersion which comprises at least one cellulose ether as described above and additionally at least one active ingredient that has a Tm/Tg ratio of more than 1.0 up to 1.8, preferably more than 1.1 up to 1.6, more preferably from 1.15 to 1.5, most preferably from 1.25 to 1.40, wherein the melting temperature Tm and the glass transition temperature Tg each are in Kelvin. The active ingredient preferably has a log P of more than 1 up to 11, preferably 1.5 to 8, most preferably 2 to 6.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 1 to 40 weight percent, more preferably from 2.5 to 30 weight percent, most preferably from 5 to 30 weight percent, and particularly from 7 to 30 percent of at least one cellulose ether as described above, from 40 to 99 weight percent, more preferably from 54.9 to 97.4 weight percent, most preferably from 65 to 94.5 weight percent and particularly from 60 to 90 percent of i) an organic liquid diluent or ii) an organic diluent blended with a minor amount of water, e.g. an amount of water described further above, and from 0 to 40 percent, preferably from 0.1 to 40 percent, most preferably from 0.5 to 25 percent, and particularly from 3 to 15 percent of an active ingredient, based on the total weight of the liquid composition.

In one aspect of the invention the liquid composition of the present invention comprising at least one cellulose ether as described above, one or more active ingredients and optionally one or more adjuvants can be used in liquid form, for example in the form of a suspension, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with minor amounts of water as described above.

In another aspect of the invention the liquid composition of the present invention is used for producing a solid dispersion comprising at least one active ingredient, such as a drug described further above, in at least one cellulose ether as described above and optionally one or more adjuvants. The solid dispersion is produced by removing the liquid diluent from the composition. The liquid diluent is the liquid organic diluent, optionally blended with a minor amount of water as described above; i.e., when the composition comprises water as an optional additive, organic liquid diluent and water are removed from the liquid composition to prepare the solid dispersion of the present invention.

One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25.

In another aspect of the invention the liquid composition of the present invention may be used for coating dosage forms, such as tablets, granules, pellets, caplets, lozenges, suppositories, pessaries or implantable dosage forms, to form a coated composition. If the liquid composition of the present invention comprises an active ingredient, such as a drug, drug layering can be achieved, i.e., the dosage form and the coating may comprise different active ingredients for different end-uses and/or having different release kinetics.

In yet another aspect of the invention the liquid composition of the present invention may be used for the manufacture of capsules in a process which comprises the step of contacting the liquid composition with dipping pins.

Alternatively, the solid dispersion of the present invention may be prepared by i) blending a) at least one cellulose ether defined above, b) one or more active ingredients and c) one or more optional additives, and ii) subjecting the blend to extrusion. The term "extrusion" as used herein includes processes known as injection molding, melt casting and compression molding. Techniques for extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for extrusion, preferably melt-extrusion. Useful devices for extrusion, specifically useful extruders, are known in the art. Alternatively, the components a), b) and optionally c) may be fed separately into the extruder and blended in the device before or during a heating step. Preferably components a), b) and optionally c) are pre-blended in an extruder feeder and fed from there into the extruder. The composition or the components that has or have been fed into an extruder are passed through a heated area of the extruder at a temperature which will melt or soften the composition or at least one or more components thereof to form a blend throughout which the active ingredient is dispersed. The blend is subjected to extrusion and caused to exit the extruder. Typical extrusion temperatures are from 50 to 210° C., preferably from 70 to 200° C., more preferably from 90 to 190° C., as determined by the setting for the extruder heating zone(s). An operating temperature range should be selected that will minimize the degradation or decomposition of the active ingredient and other components of the composition during processing. Single or multiple screw extruders, preferably twin screw extruders, can be used in the extrusion process of the present invention.

The molten or softened mixture obtained in the extruder are forced through one or more exit openings, such as one or more nozzles or dies. The molten or softened mixture then exits via a die or other such element having one or a plurality of openings, at which time, the extruded blend (now called the extrudate) begins to harden. Since the extrudate is still in a softened state upon exiting the die, the extrudate may be easily shaped, molded, chopped, spheronized into beads, cut into strands, tabletted or otherwise processed to the desired physical form. The extrudate can optionally be cooled to hardening and ground into a powdered form.

The solid dispersion of the present invention preferably comprises from 20 to 99.9 percent, more preferably from 30 to 98 percent, and most preferably from 60 to 95 percent of a cellulose ether a) as described above, and preferably from 0.1 to 80 percent, more preferably from 2 to 70 percent, and most preferably from 5 to 40 percent of an active ingredient b), based on the total weight of the cellulose ether a) and the active ingredient b). The combined amount of the cellulose ether a) and the active ingredient b) is preferably at least 60 percent, more preferably at least 70 percent, and most preferably at least 80 percent, based on the total weight of the solid dispersion. The remaining amount, if any, are one or more of the adjuvants c) as described below. The solid dispersion can comprise one or more of the cellulose ethers a), one or more of the active ingredients b), and optionally one or more of the adjuvants c), however their total amount is generally within the above-mentioned ranges.

Once the solid dispersion comprising at least one active ingredient in at least one cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms, such as tablets, pills, granules, pellets, caplets microparticles, fillings of capsules, or into pastes, creams, suspensions or slurries. The amount of the active ingredient in the dosage form is generally is at least 0.1 percent, preferably at least 1 percent, more preferably at least 3 percent, most preferably at least 5 percent and generally up to 70 percent, or up to 50 percent, or up to 30 percent, or up to 25 percent, based on the total weight of the dosage form.

The liquid composition and the solid dispersion of the present invention may further comprise optional additives, such as coloring agents, pigments, opacifiers, flavor and taste improvers, antioxidants, plasticizers, surfactants, lubricants, anti-tack agents, glidants, fillers, disintegrants, binders, salts, such as sodium chloride; saccharides, such as white sugar and lactose; a second cellulose ether, and any combination thereof. Optional additives are preferably pharmaceutically acceptable. Useful amounts and types of one or more optional adjuvants are generally known in the art and depend on the intended end-use of the liquid composition or the solid dispersion of the present invention. A large variety of optional adjuvants is disclosed in International Patent Application WO 2005/115330, page 45, line 20-page 46, line 33.

The following examples are for illustrative purposes only and are not intended to limit the scope of the present invention. All percentages are by weight unless otherwise specified.

Examples 1 and 2 and Comparative Example A

The determination of the % methoxyl and % hydroxypropoxyl in hydroxypropyl methylcellulose (HPMC) was carried out according to the United States Pharmacopeia (USP 35, "Hypromellose", pages 3467-3469). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the HPMC samples was measured as a 2.0% by weight solution in water at 20° C. The 2.0% by weight HPMC solution in water was prepared according to United States Pharmacopeia (USP 35, "Hypromellose", pages 3467-3469) followed by an Ubbelohde viscosity measurement according to DIN 51562-1:1999-01 (January 1999).

TABLE 1

| (Comparative) Example | Viscosity at 20° C.[1] | DS (methyl) | MS (hydroxypropyl) | % methoxyl | % hydroxypropoxyl |
|---|---|---|---|---|---|
| 1 | 2.25 | 1.91 | 0.23 | 29.1 | 8.6 |
| A | 3.1 | 1.85 | 0.25 | 28.2 | 9.3 |
| 2 | 2.18 | 1.87 | 0.16 | 29.3 | 6.0 |

[1]measured as 2.0 weight percent solution in water

Storage Stability

To evaluate the storage stability of a liquid composition of the present invention and of a comparative liquid composition, 10 weight percent of the HPMC of Examples 1 and 2 and of Comparative Example A each were separately dissolved in Solution I): a mixture of methanol/water having a weight ratio of 90/10 at room temperature for 2 hours, Solution II): a mixture of methanol/water having a weight ratio of 90/10 and additionally comprising 0.4 wt.-% of NaOH, based on the total weight of the methanol/water mixture at room temperature for 2 hours.

The complex viscosity |η*| of the mixtures comprising the HPMC at 25° C. was investigated in a time sweep experiment using an Anton Paar Physica UDS200 rheometer (Ostfildern, Germany) in oscillation shear flow. A Cup & Bob (Z3-DIN) geometry was used and the upper surface of the geometry was covered with small metal sheets to avoid evaporation. The measurements were performed at a constant frequency of 1 Hz and a constant strain (deformation amplitude) of 0.5% over 18 h in the linear visco-elastic region. These measurements were conducted with a data collection rate of one average value each 5 minutes.

The results are summarized in Table 2 below. These results, in particular the comparison between Example 1 and Comparative Example A, illustrate that a liquid composition comprising an above-described cellulose ether having a viscosity of up to 2.33 mPa·s, measured as a 2 wt.-% solution in water at 20° C., is much more storage stable and exhibits a much smaller viscosity increase after storage of the liquid composition over an extended time period than a liquid composition comprising an organic liquid diluent and a comparable cellulose ether having a higher viscosity, measured as a 2 wt.-% solution in water at 20° C.

TABLE 2

| complex viscosity \|η *\|at x min. [mPa•s] | 10 wt. % of HPMC of Example 1 in | | 10 wt. % of HPMC of Comp. Example A in | | 10 wt. % of HPMC of Example 2 in | |
|---|---|---|---|---|---|---|
| | Solution I | Solution II | Solution I | Solution II | Solution I | Solution II |
| 5 | 509 | 347 | 394 | 414 | 614 | 475 |
| 30 | 549 | 420 | 429 | 751 | 816 | 716 |
| 60 | 598 | 508 | 559 | 455 | 1000 | 1240 |
| 120 | 600 | 539 | 611 | 512 | 1190 | 1040 |
| 180 | 653 | 577 | 657 | 535 | 1360 | 1260 |
| 240 | 694 | 622 | 665 | 553 | 1490 | 1540 |
| 300 | 685 | 586 | 699 | 586 | 1600 | 1450 |
| 360 | 740 | 672 | 727 | 701 | 1690 | 1540 |
| 420 | 748 | 693 | 733 | 706 | 1770 | 1560 |
| 480 | 763 | 684 | 744 | 1150 | 1830 | 1590 |
| 540 | 765 | 718 | 777 | 7110 | 1890 | 1640 |
| 600 | 774 | 759 | 846 | 88200 | 1950 | 1670 |
| 660 | 775 | 770 | 2120 | 383000 | 1990 | 1700 |
| 720 | 808 | 768 | 51900 | 615000 | 2050 | 1780 |
| 780 | 843 | 791 | 1730000 | 1310000 | 2110 | 1820 |
| 840 | 866 | 763 | 3660000 | 1820000 | 2140 | 1820 |
| 900 | 880 | 811 | 4340000 | 2660000 | 2180 | 1840 |
| 960 | 897 | 810 | 4970000 | 2740000 | 2210 | 1880 |
| 1020 | 925 | 810 | 4650000 | 3300000 | 2370 | 1910 |
| 1080 | 935 | 827 | 5870000 | 4040000 | 2110 | 1850 |

Impact of Cellulose Ethers on the Aqueous Solubility of a Poorly Soluble Drug

The ability of the cellulose ethers of Examples 1 and 2 and of Comparative Example A to maintain drug concentrations in an aqueous solution at supersaturation levels was tested with the poorly water soluble drugs Griseofulvin and Phenytoin.

Griseofulvin has a water solubility of 8.54 mg/l, a log P of 2.2, a Tm of 220° C., a Tg of 85° C., and, accordingly a Tm/Tg=493° K/358° K=1.39. [Feng, Tao et. al.; J. Pharm. Sci.; Vol. 97, No. 8, 2008, pg 3207-3221 and W. Curatolo, Pharmaceutical Research, Vol. 26, No. 6, June 2009, pg 1422]. Griseofulvin belongs to group 2 on the map Tm/Tg ratio versus log P (FIG. 14 on page 1018 in MOLECULAR PHARMACEUTICS VOL. 5, NO. 6).

Phenytoin has a water solubility of 32 mg/l, a log P of 2.47, a Tm of 295° C., a Tg of 71° C. and, accordingly a Tm/Tg=568° K/344° K=1.65 [Friesen et al., MOLECULAR PHARMACEUTICS VOL. 5, NO. 6, 1003-1019 and W. Curatolo, Pharmaceutical Research, Vol. 26, No. 6, June 2009, pg 1422]. Phenytoin belongs to group 3 on the map Tm/Tg ratio versus log P (FIG. 14 on page 1018 in MOLECULAR PHARMACEUTICS VOL. 5, NO. 6, 2008).

Solutions of a cellulose ether listed in Table 3 below (950 µl, 3.16 mg/L) in phosphate buffered saline (82 mM sodium chloride, 20 mM sodium phosphate dibasic, 47 mM potassium phosphate monobasic, 0.5 wt % simulated intestinal fluid powder, pH 6.5) at 37° C. were robotically delivered into designated 1 mL vials arranged in an aluminum 96 (8×12) well block heated to 37° C. using a Tecan 150 liquid handler. Organic drug solutions at 37° C. were dispensed onto the phosphate buffered saline aqueous solution comprising a cellulose ether listed in Table 3 below. The organic drug solution was a) 20 g/L griseofulvin in dimethylformamide, 50 µL, final maximum drug concentration of 1000 mg/L, or b) 20 g/L phenytoin in dimethylformamide, 50 µL, final maximum drug concentration of 1000 mg/L. The robot aspirated and dispensed liquid in a set sequence for each vial for about 30 s to mix. After 180 minutes the vials were centrifuged for 1 mM at about 3200×g (g=gravitational force on earth). An aliquot (30 µl) was transferred to methanol (150 µl) in a 96-well plate, sealed, briefly gently agitated to mix, and then the drug concentration was analyzed by HPLC.

In a Control Run the experiment was repeated with a phosphate buffered saline aqueous solution which did not contain any amount of cellulose ether.

In Table 3 below the concentrations of Griseofulvin and Phenytoin are listed that have not precipitated upon centrifugation after 180 minutes but that remain dissolved in the phosphate buffered saline aqueous solution.

The results in Table 3 below illustrate that the cellulose ethers comprised in the liquid compositions and in the solid dispersions of the present invention are able to maintain the concentration of poorly water-soluble drugs in an aqueous solution at supersaturation levels. A considerably higher drug concentration in an aqueous solution can be maintained by the cellulose ethers comprised in the liquid compositions and in the solid dispersions of the present invention than in the Control Run in the absence of a cellulose ether. Moreover, substantially the same or only a slightly lower drug concentration in an aqueous solution can be maintained by the cellulose ethers of Examples 1 and 2, as compared to the cellulose ether of Comparative Example A, but organic solutions comprising the cellulose ethers of Examples 1 and 2 are much more storage stable.

TABLE 3

| (Comparative) Example | Viscosity at 20° C. [mPa · s][1] | DS (methyl) | MS (hydroxypropyl) | Griseofulvin concentration [mg/L] at 180 min. | Phenytoin concentration [mg/L] at 180 min. |
|---|---|---|---|---|---|
| 1 | 2.25 | 1.91 | 0.23 | 465 | 231 |
| A | 3.1 | 1.85 | 0.25 | 468 | 269 |
| 2 | 2.18 | 1.87 | 0.16 | 453 | 212 |
| Control | — | — | — | 177 | 71 |

[1]measured as 2.0 weight percent solution in water

The invention claimed is:

1. A process for producing a solid dispersion comprising at least one active ingredient in at least one water-soluble non-ionic cellulose ether having a viscosity of from 1.20 to 2.33 mPa·s, measured as a 2 wt.-% solution in water at 20° C.,
  comprising the steps of blending a) at least one water-soluble non-ionic cellulose ether having a viscosity of from 1.20 to 2.33 mPa·s, measured as a 2 wt.-% solution in water at 20° C., b) at least one active ingredient and c) one or more optional additives, and subjecting the blend to extrusion at a temperature of from 90 to 190° C.,
  wherein the water-soluble non-ionic cellulose ether is a hydroxypropyl methylcellulose having a DS(methyl) of from 1.0 to 2.5 and an MS(hydroxypropyl) of from 0.05 to 0.90 or a methylcellulose having a DS(methyl) of from 1.0 to 2.5.

2. The process of claim 1 wherein the water-soluble non-ionic cellulose ether has a viscosity of from 1.20 to 2.26 mPa·s, measured as a 2 wt.-% solution in water at 20° C.

3. The process of claim 1 wherein the hydroxypropyl methylcellulose has a DS(methyl) of from 1.1 to 2.2 and the methylcellulose has a DS(methyl) of from 1.1 to 2.2.

4. The process of claim 3 wherein the hydroxypropyl methylcellulose has a DS(methyl) of from 1.6 to 2.05 and the methylcellulose has a DS(methyl) of from 1.6 to 2.05.

5. The process of claim 1 wherein the hydroxypropyl methylcellulose has an MS(hydroxypropyl) of from 0.12 to 0.60.

6. The process of claim 5 wherein the hydroxypropyl methylcellulose has an MS(hydroxypropyl) of from 0.12 to 0.50.

7. The process of claim 1 wherein the water-soluble non-ionic cellulose ether is a hydroxypropyl methylcellulose having a DS(methyl) of from 1.6 to 2.05 and an MS(hydroxypropyl) of from 0.12 to 0.50.

8. The process of claim 2 wherein the water-soluble non-ionic cellulose ether is a hydroxypropyl methylcellulose having a DS(methyl) of from 1.6 to 2.05 and an MS(hydroxypropyl) of from 0.12 to 0.50.

9. The process of claim 1 wherein the water-soluble non-ionic cellulose ether is a methylcellulose having a DS(methyl) of from 1.0 to 2.5.

10. The process of claim 1 wherein the active ingredient is a drug having an aqueous solubility of 0.5 mg/mL or less.

11. The process of claim 1 wherein the components a), b) and optionally c) are blended in the form of particles.

* * * * *